United States Patent
Ingimundarson et al.

(10) Patent No.: US 8,292,838 B2
(45) Date of Patent: Oct. 23, 2012

(54) ORTHOPEDIC DEVICE HAVING ANTEROPOSTERIOR ARTICULATION

(75) Inventors: Arni Thor Ingimundarson, Ladera Ranch, CA (US); Ashley Kimes, Irvine, CA (US)

(73) Assignee: Ossur HF, Reykjavik (IS)

( * ) Notice: Subject to any disclaimer, the term of this patent is extended or adjusted under 35 U.S.C. 154(b) by 556 days.

(21) Appl. No.: 12/264,020

(22) Filed: Nov. 3, 2008

(65) Prior Publication Data
US 2009/0118656 A1    May 7, 2009

Related U.S. Application Data

(60) Provisional application No. 60/996,150, filed on Nov. 5, 2007, provisional application No. 61/071,535, filed on May 5, 2008.

(51) Int. Cl.
| | |
|---|---|
| *A61F 5/37* | (2006.01) |
| *A61F 13/00* | (2006.01) |
| *A61F 5/00* | (2006.01) |
| *A61F 13/06* | (2006.01) |
| *A61B 19/00* | (2006.01) |

(52) U.S. Cl. ............... 602/26; 602/5; 602/16; 602/23; 602/60; 602/61; 602/62; 128/846; 128/869; 128/882

(58) Field of Classification Search ............... 602/5, 16, 602/23, 26, 60, 61, 62; 128/846, 869, 882; 606/53, 54
See application file for complete search history.

(56) References Cited

U.S. PATENT DOCUMENTS

| | | | | |
|---|---|---|---|---|
| 4,805,606 | A | * | 2/1989 | McDavid, III ............... 602/26 |
| 5,277,698 | A | | 1/1994 | Taylor |
| 5,302,169 | A | | 4/1994 | Taylor |
| 5,383,845 | A | * | 1/1995 | Nebolon ............... 602/26 |
| 5,400,806 | A | | 3/1995 | Taylor |
| 5,457,891 | A | | 10/1995 | Taylor |
| 5,562,605 | A | * | 10/1996 | Taylor ............... 602/26 |
| 5,669,873 | A | | 9/1997 | Towsley |
| 5,797,864 | A | * | 8/1998 | Taylor ............... 602/26 |
| 6,027,466 | A | * | 2/2000 | Diefenbacher et al. ......... 602/16 |
| 6,565,523 | B1 | * | 5/2003 | Gabourie ............... 602/16 |
| 6,960,177 | B2 | * | 11/2005 | Turrini et al. ............... 602/26 |
| 6,981,957 | B2 | * | 1/2006 | Knecht et al. ............... 602/26 |
| 7,001,349 | B2 | | 2/2006 | Vollbrecht et al. |
| 7,198,610 | B2 | | 4/2007 | Ingimundarson et al. |
| 7,201,728 | B2 | | 4/2007 | Sterling |
| 7,473,236 | B1 | * | 1/2009 | Mathewson ............... 602/62 |
| 7,597,675 | B2 | * | 10/2009 | Ingimundarson et al. ...... 602/26 |
| 7,713,225 | B2 | * | 5/2010 | Ingimundarson et al. ...... 602/26 |
| 7,794,416 | B2 | * | 9/2010 | Besselink et al. ............... 602/16 |
| 7,794,418 | B2 | * | 9/2010 | Ingimundarson et al. ...... 602/26 |

(Continued)

FOREIGN PATENT DOCUMENTS

EP    1 302 184    4/2003

(Continued)

*Primary Examiner* — Patricia Bianco
*Assistant Examiner* — Brandon L Jackson
(74) *Attorney, Agent, or Firm* — Bacon & Thomas, PLLC

(57) ABSTRACT

An orthopedic device in the form of an unloading osteoarthritic knee brace has proximal and distal frame members with a flexion-extension hinge positioned between the proximal and distal frame members. At least one articulating free hinge is positioned in an upright between the flexion-extension hinge and one of the proximal and distal frame members. The free hinge provides free rotation of the proximal or distal frame member about the anteroposterior axis with respect to the flexion-extension hinge.

18 Claims, 8 Drawing Sheets

U.S. PATENT DOCUMENTS

| | | |
|---|---|---|
| 7,896,827 B2 * | 3/2011 | Ingimundarson et al. ...... 602/26 |
| 2004/0068215 A1 * | 4/2004 | Adelson et al. ................. 602/26 |
| 2004/0267179 A1 | 12/2004 | Lerman |
| 2005/0192523 A1 | 9/2005 | Knetch et al. |
| 2006/0135902 A1 * | 6/2006 | Ingimundarson et al. ...... 602/26 |
| 2006/0167394 A1 | 7/2006 | Ceriani et al. |
| 2008/0188784 A1 * | 8/2008 | Ceriani et al. .................. 602/16 |

FOREIGN PATENT DOCUMENTS

| | | |
|---|---|---|
| WO | WO 01/21114 A1 | 3/2001 |
| WO | WO 03/103547 | 12/2003 |
| WO | WO 2006/078428 | 7/2006 |

* cited by examiner

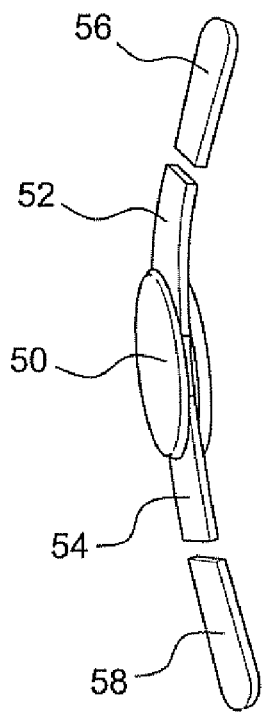
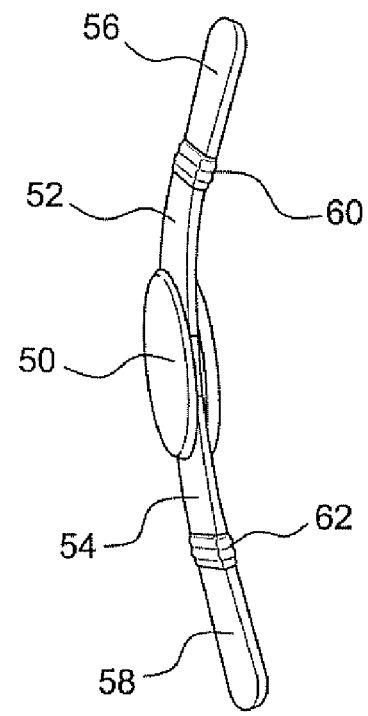
FIG. 4  FIG. 5
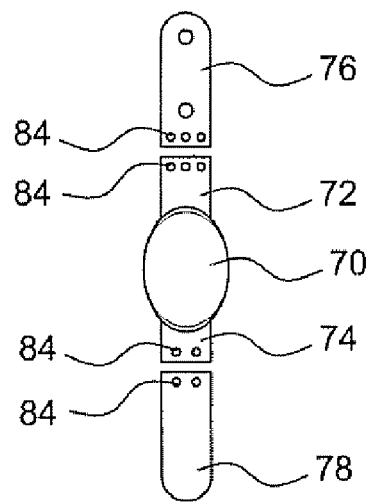
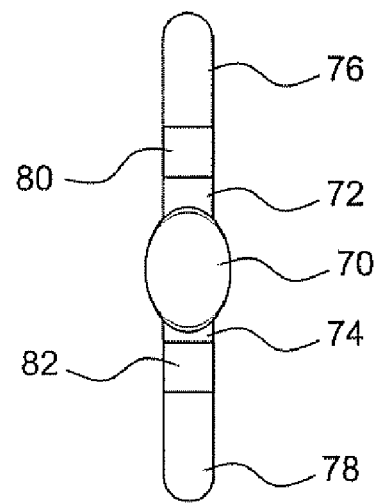
FIG. 6  FIG. 7

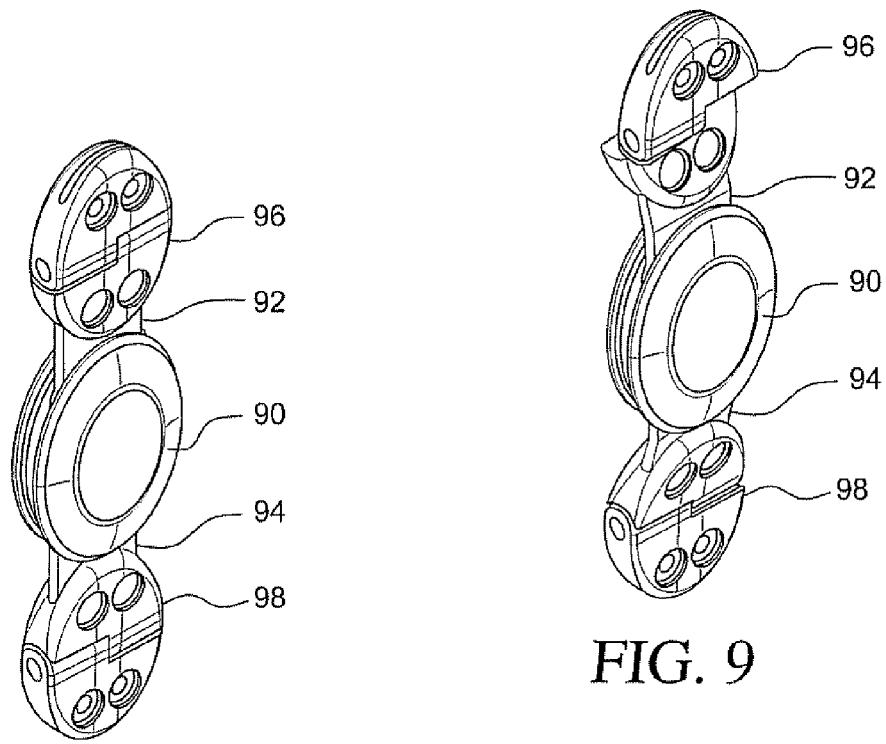
FIG. 8
FIG. 9
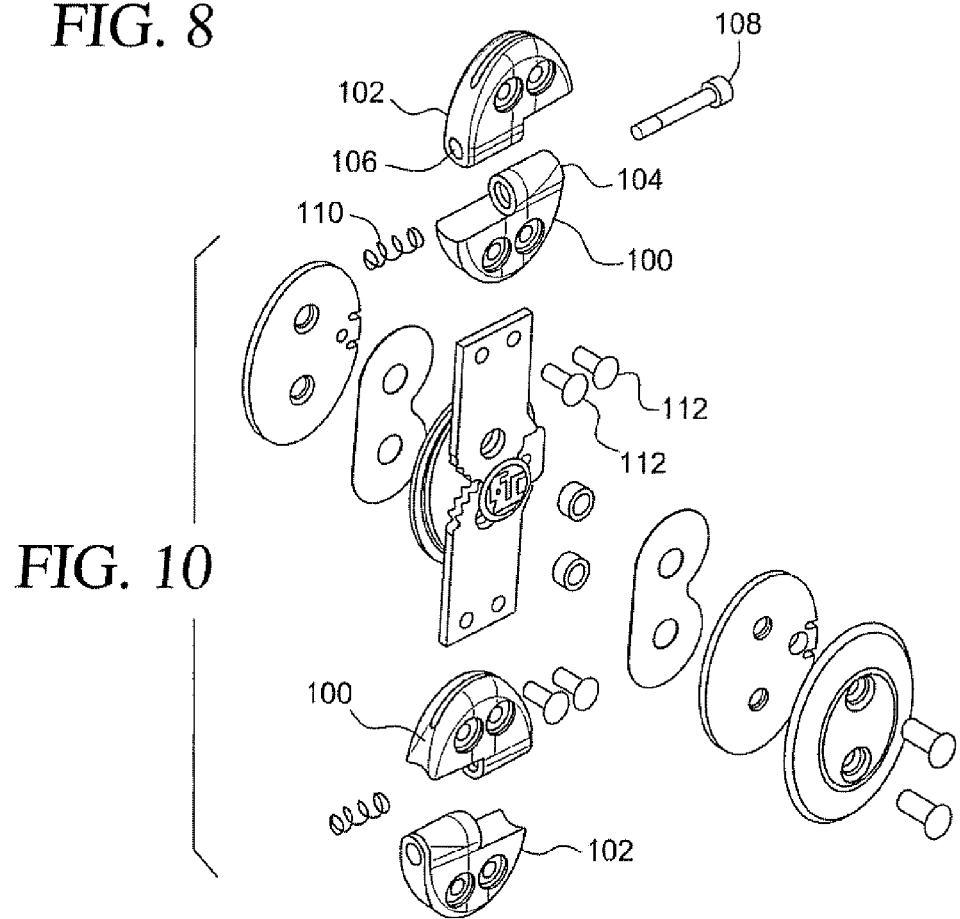
FIG. 10

ORTHOPEDIC DEVICE HAVING ANTEROPOSTERIOR ARTICULATION

This application claims the benefit of U.S. Provisional Application No. 60/996,150, filed Nov. 5, 2007, and U.S. Provisional Application No. 61/071,535, filed May 5, 2008.

FIELD OF THE INVENTION

The present invention relates generally to the field of orthopedic and prosthetic devices, and more particularly to an orthopedic device that provides stability, protection, support, rehabilitation, and/or unloading to a portion of the human anatomy,

BACKGROUND

Knee braces are widely used to treat a variety of knee infirmities. Such braces may be configured to impart forces or leverage on the limbs surrounding the knee joint in order to relieve compressive forces within a portion of the knee joint, or to reduce the load on that portion of the knee. Moreover, in the event that knee ligaments are weak and infirm, a knee brace may stabilize, protect, support, unload, and/or rehabilitate the knee.

The knee is acknowledged as one of the weakest joints in the body, aid serves as the articulating joint between the thigh and calf muscle groups. The knee is held together primarily by small but powerful ligaments. Knee instability arising out of cartilage damage, ligament strain and other causes is relatively commonplace since the knee joint is subjected to significant loads during the course of almost any kind of physical activity requiring the use of the legs.

A healthy knee has an even distribution of pressure in both the medial and lateral compartments of the knee. It is normal for a person with a healthy knee to place a varus moment on the knee when standing so that the pressure between the medial and lateral compartments is uneven but still natural.

One type of knee infirmity that many individuals are prone to having is compartmental osteoarthritis. Compartmental osteoarthritis may arise when there is a persistent uneven distribution of pressure in one of the medial and lateral compartments of the knee. Compartmental osteoarthritis can be caused by injury, obesity, misalignment of the knee, or simply due to aging of the knee.

A major problem resulting from osteoarthritis of the knee is that the smooth cartilage lining the inside of the knee wears away. This leads to a narrowing of the joint space with the development of cysts and erosions in the bone ends. Because of the narrowing of the joint, bone comes directly in contact with bone, and an uneven distribution of pressure develops across the knee which may result in the formation of bone spurs around the joint. All of these changes ultimately lead to increasing pain and stiffness of the joint.

While there are no cures to osteoarthritis, there are many treatments. Individuals who have a diagnosis of isolated medial or lateral compartmental osteoarthritis of the knee are confronted with a variety of treatment options such as medications, surgery, and nonsurgical interventions. Nonsurgical interventions include the use of canes, lateral shoe wedges, and knee bracing.

Knee bracing is useful to provide compartmental pain relief by reducing the load on the affected compartment through the application of an opposing external valgus or varus moment about the knee joint. Unloading knee braces have been shown to significantly reduce osteoarthritis knee pain while improving knee function. Typically, however, the amount of varus and/or valgus rotation that a brace may provide is limited by the use of rigid or substantially rigid supporting struts or frames. While some brace designs do allow for selective, fixed adjustment of the amount of varus and/or valgus rotation provided by the brace, the disclosed embodiments provide an unexpected result of freely adjusting varus and/or valgus rotation for a brace while utilizing the geometry of the leg and the straps of the brace to selectively adjust the varus and/or valgus rotation of the leg for a desired effect.

While known knee braces are successful at reducing pain or at stabilizing a knee joint, many users find these braces to be bulky, difficult to don, complicated to configure, and uncomfortable to wear. For these reasons, the embodiments described herein have streamlined features capable of providing relief for medial or lateral compartmental osteoarthritis, or functional stability of the knee while providing a configuration that has a low profile and unexpectedly provides a more conforming and supportive fit for the orthopedic device.

SUMMARY

The orthopedic device disclosed herein may be of an unloading type knee brace, in accordance with the principles described in U.S. Pat. No. 7,198,610, granted Apr. 3, 2007, and U.S. Pat. No. 5,277,698, granted Jan. 11, 1994, both incorporated herein in their entirety by reference.

A knee brace in accordance with the present disclosure utilizes articulating portions in the form of free hinges in the uprights or struts of the knee brace to provide free varus/valgus rotation of the proximal and distal (also referred to as first and second) frame members (or shells) with respect to the flexion-extension hinge of the knee brace. The articulating portions allow the upright components and the frame members connected thereto to freely rotate about an anteroposterior axis with respect to the flexion-extension hinge. In other words, the articulating portion is not lockable or fixable, but instead allows the components to freely rotate within a predetermined range of motion.

This configuration provides the unexpected results that when the knee brace is positioned on the leg and the one or more stability straps are tightened, the varus/valgus angle of the knee may be adjusted independently of the flexion-extension hinge element without compressing and binding the hinge element. Further, the desired angle of varus/valgus rotation of the knee joint may be altered by adjustment of the one or more stability straps, in combination with the use of the free hinges. The desired angle of varus/valgus rotation can be altered by adjusting the one or more stability straps. There may also be some variation in the varus/valgus angle due to the change in the alignment of the leg through the gait cycle, in so far as the free hinges allow the proximal and distal frame members to move with the leg when the alignment of the leg changes.

These relationships are contrary to what a skilled artisan in the field of orthopedic braces, and in particular knee braces, would anticipate. In particular, a skilled artisan would expect such a configuration to cause the proximal and distal frame members to compress together, the flexion-extension hinge to bind-up, or the components of the brace to otherwise obtain an ineffectual orientation. The anticipated ineffectual orientation would appear to arise due to the diagonal forces of the one or more stability straps acting to bring the proximal and distal shells closer together, thus reducing the function and stability of the knee brace or undesirably altering the amount of varus/valgus rotation.

These particular effects do not in fact occur, but rather, unexpectedly, the utilization of the articulating free hinges provides great flexibility in adjusting varus/valgus angles of the knee, while maintaining the structural support and functionality required of a knee brace, and further enhancing the conformity and fit of the brace to the leg. This is due to the fact that there is a single free point above and a single free point below the flexion-extension hinge element. The use of a single free point above and below the hinge element does not allow the proximal and distal frame members to compress together, but instead allows them to move only with varus/valgus movement. Thus, the flexion-extension hinge element acts to maintain the proximal and distal frame members spaced from each other, even when the one or more stability straps are adjusted to alter the varus/valgus angle. The flexion-extension hinge element would not function in this manner if two free points were provided above and below the hinge. In such a case, the frame members or the hinge element would collapse, and thus would not provide suitable structural support.

As just mentioned, the varus/valgus angle is substantially set by the use of one or more stability straps. The articulating free hinges allow the proximal and distal frame members to freely rotate without locking within a predetermined range of motion about an anteroposterior axis in order to alter the varus/valgus angle when the tension of the one or more stability straps of the knee brace is adjusted. In other words, once the straps have been tightened, the varus/valgus angle may only change with the changes in the alignment of the leg. As mentioned above, the varus/valgus angle may be adjusted by altering the tension in the stability straps.

Meanwhile, since the flexion-extension hinge does not participate in providing the varus/valgus angle for the knee brace, the articulating free hinges allow the hinge element to closely conform to the leg/knee joint throughout the entire gait cycle. In other words, the upright defined by or including the flexion-extension hinge member maintains its conformity to the knee throughout the gait cycle since the articulating free hinges constantly adjust and flex with the patient during the gait cycle. In other words, the flexion-extension hinge is allowed to float in conformance with the leg during the gait cycle due to the single free point positioned above and the single free point positioned below the flexion-extension hinge, while the knee brace maintains sufficient structural support and/or unloading of the knee joint.

Accordingly, an orthopedic device in the form of a knee brace for stabilizing, protecting, supporting, unloading, and/or rehabilitating the knee is provided. The knee brace is a low profile brace utilizing articulating free hinges to allow the varus/valgus angle of the knee to be adjusted.

In a particular exemplary embodiment, the knee brace has proximal and distal shells. In the exemplary embodiment, each of the proximal and distal shells includes an extending portion along a first side thereof, which may be a lateral or medial side. A hinge member connects to the proximal and distal shells, and in the exemplary embodiment to the extending portions. The hinge member may be a monocentric or polycentric flexion-extension hinge. A first articulating portion in the form of a free hinge connects between the flexion-extension hinge member and the proximal shell to allow the proximal shell to freely rotate into varus/valgus within a predetermined range of motion about an anteroposterior axis with respect to the hinge member. A second articulating portion in the form of a free hinge connects between the flexion-extension hinge member and the distal shell to allow the distal shell to freely rotate into varus/valgus within a predetermined range of motion about an antetoposterior axis with respect to the hinge member. In this manner, the varus/valgus angle of the knee brace may be freely adjusted.

First and second stability straps or a single spiraling strap connect to the proximal and distal shells and are selectively adjustable to provide desired rotation of the proximal and distal shells about an anteroposterior axis to the proximal and distal shells with respect to the flexion-extension hinge member. In this manner, when the knee brace is positioned on the leg, the stability straps are adjusted to obtain the desired amount of varus/valgus rotation of the knee joint. The shells substantially maintain their configuration once the straps are tightened, although some variation may occur during the gait cycle due to changes in the alignment of the leg. The varus/valgus angle of the knee can be further adjusted by the additional adjustment of the stability straps, which adjustment allows the shells to rotate about the free hinges to another configuration and to stabilize in the new configuration in order to provide a desired varus/valgus rotation to the knees.

In an exemplary embodiment, the first and second articulating free hinges each include a hinge support portion connecting to the hinge member and a frame or shell support portion connecting to the respective frame or shell members. In a variation, the shell support portion may be a portion of the shell itself or otherwise integrally formed with the shell. A resilient portion connects the hinge and shell support portions to allow the hinge and shell support portions to flex with respect to each other. The flexure occurs about an anteroposterior axis, but as an alternative, flexure may also occur about both an anteroposterior axis and the proximal-distal axis. In one embodiment, the resilient portion is an overmolded portion that encompasses at least a portion of each of the hinge and shell support portions.

In a variation, the first and second articulating free hinges each include a hinge support portion connecting to the hinge member and a shell support portion connecting to the respective shell members. A pivoting portion connects the hinge and shell support portions to allow the hinge and shell support portions to pivot with respect to each other. In one embodiment, the pivot portion includes a first connection member connecting to the hinge support portion and a second connection member connecting to the shell support portion. A pivot pin connects the first and second connection members in a freely pivotable manner. In a further variation, one or both of the free hinges can be locked in a specific orientation if a patient requires additional medial-lateral stability.

While the articulating free hinges allow the proximal and distal shells to freely rotate about an anteroposterior axis with respect to the hinge member, once the brace is positioned on the leg and the stability straps are tightened the shells substantially obtain a specified configuration for providing varus/valgus rotation to the knee. Contrary to expectations, the free hinges do not allow the shells to collapse about the flexion-extension hinge element or otherwise obtain a different orientation unless the alignment of the leg changes.

Thus, the configuration of the knee brace allows the brace to self align to any leg shape by allowing the flexion-extension hinge to float and thus closely conform to the leg via the single pivot point above and the single pivot point below the hinge element. Once the one or more stability straps are tightened, the upright including the hinge element, while still allowing flexion and extension of the knee, forms a substantially rigid and robust support against or along the leg due to the interaction of the diagonal forces of the stability straps that are applied to the shells and the internal support of the leg against the inside of the brace. Thus, the forces of the stability straps are focused on providing the varus/valgus angle and the unloading of the knee joint.

The support provided by the upright and the hinge element to the leg is maintained so long as the anatomy or alignment of the leg doesn't change. Accordingly, once the one or more stability straps are tightened, a lateral or medial force applied to the flexion-extension hinge element will not produce movement of the hinge. The flexion-extension hinge element does move with the leg when the alignment of the leg changes throughout the gait cycle due to the single free point provided above and the single free point provided below the hinge. For each particular point in the gait cycle, however, if movement of the leg is frozen, the upright including the hinge element feels substantially rigid against the leg and is not subject to medial-lateral movement.

In an alternate configuration of a knee brace, one of the proximal or distal articulating free hinges may be locked at a particular varus/valgus angle, or a single free hinge may be provided either proximally or distally of the flexion-extension hinge. In this manner, the knee brace still provides adjustability for the varus/valgus angle of the knee, while incorporating increased rigidity, thus obtaining benefits of both the free hinge brace configuration and a rigid strut brace configuration.

The numerous other advantages, features and functions of embodiments of an orthopedic device will become readily apparent and better understood in view of the following description and accompanying drawings. The following description is not intended to limit the scope of the orthopedic device, but instead merely provides exemplary embodiments for ease of understanding.

BRIEF DESCRIPTION OF THE DRAWINGS

These and other features, aspects, and advantages of the present invention will become better understood with regard to the following description, appended claims, and accompanying drawings where:

FIG. 4 is a perspective view of a partially completed hinge assembly for use with the knee brace of FIG. 1;

FIG. 5 is a perspective view of the completed hinge assembly of FIG. 4;

FIG. 6 is a front view of another partially completed hinge assembly for use with the knee brace of FIG. 1;

FIG. 7 is a front view of the completed hinge assembly of FIG. 6;

FIG. 8 is a perspective view of yet another hinge assembly for use with the knee brace of FIG. 1;

FIG. 9 is a perspective view of a variation of the hinge assembly of FIG. 8;

FIG. 10 is an exploded view of the hinge assembly of FIG. 8;

Figure 1:
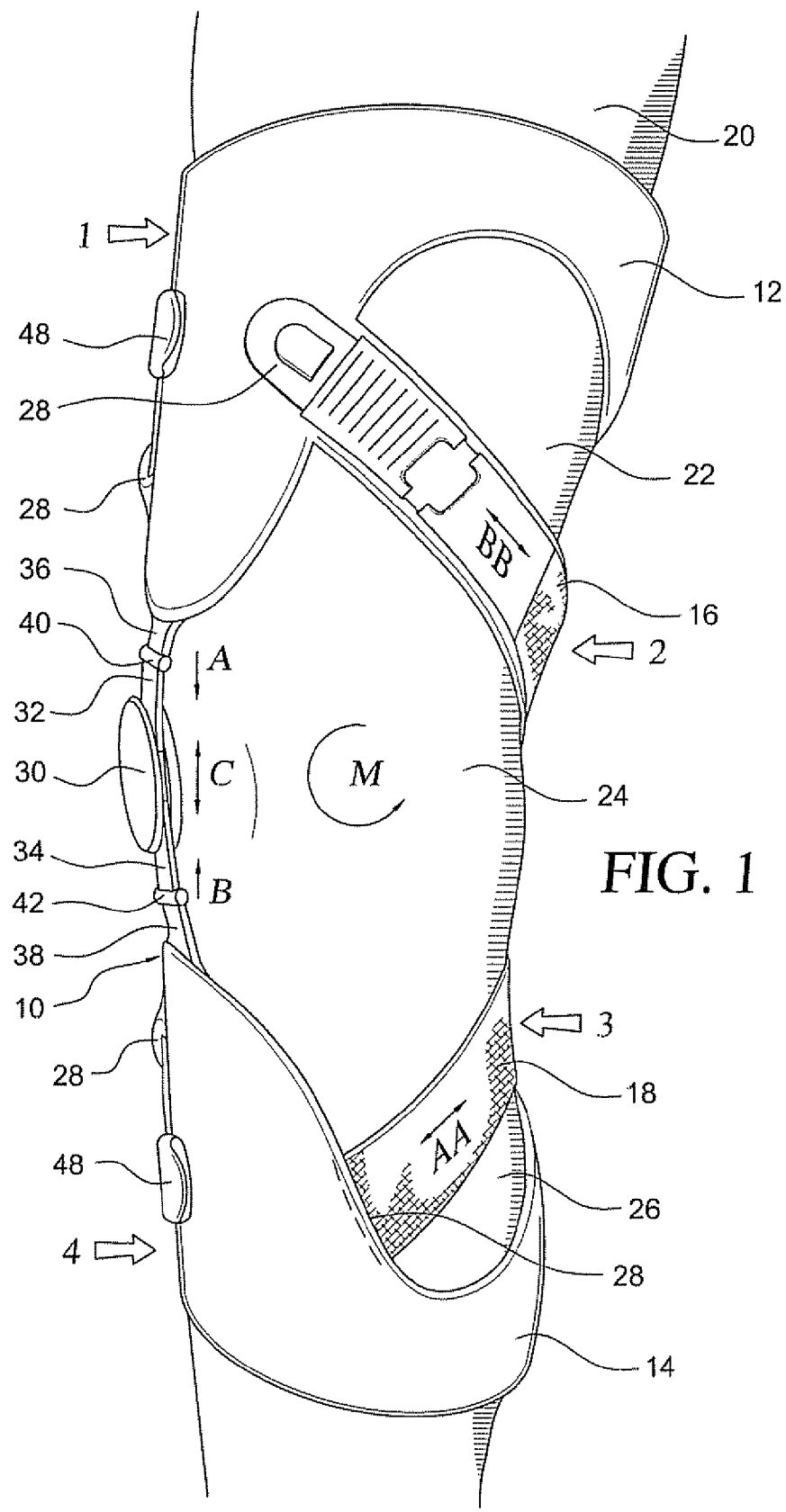
FIG. 1 is a front perspective view of an embodiment of a knee brace according to the present disclosure.

It should be noted that the drawing figures are not necessarily drawn to scale, but instead are drawn to provide a better understanding of the components thereof and are not intended to be limiting in scope, but rather to provide exemplary illustrations. It should further be noted that the figures illustrate exemplary embodiments of a knee brace and the components thereof, and in no way limit the structures or configurations of a knee brace and components thereof according to the present disclosure.

DETAILED DESCRIPTION

A. Environment and Context

An embodiment of an orthopedic device is provided to reduce the effect of osteoarthritis in a knee joint, or stabilize a knee joint that has been weakened by injury or other infirmities. Although the illustrated embodiment shows the flexion-extension hinge positioned on the lateral side of the orthopedic device and the stability straps positioned on the medial side of the orthopedic device, it will be understood that the orthopedic device may be configured to reduce or cure both medial and lateral knee joint infirmities, and thus, the hinge may be positioned on the medial side of the orthopedic device and the stability straps may be positioned on the lateral side of the orthopedic device. Further, flexion-extension hinges may also be positioned on both the lateral and medial sides of the orthopedic device, however, in the exemplary embodiment a single flexion-extension hinge and the associated upright with free hinges surprisingly provides sufficient stability aid support to the knee joint, without the need for additional rigid supports on the opposing side of the knee brace.

The use of the phrases "freely rotatable," "free rotation," and variations thereof (including "free hinge") means that there is the ability for continuous, non-fixable, non-lockable rotation within a predetermined range of motion. In other words, "freely rotatable," "free rotation," and variations thereof mean that there is no hindrance to rotation, such as a fixing or locking mechanism, and thus, components are free to rotate within a predetermined range of motion. Exemplary predetermined ranges within which components can freely rotate are, within nearly 360 degrees, within generally 270 degrees, within generally 180 degrees, within generally 90 degrees, within generally 45 degrees, and within generally 15 degrees. Of course, any suitably desired predetermined range may be utilized. The usage of the words generally or nearly in the context of this applications allow for variations due to tolerances, or other recognized manifestations of inherent limitations on achieving perfect ranges of rotation.

The embodiment of the disclosure is particularly adapted for a human knee joint, and may be dimensioned to accommodate different types, shapes and sizes of human joints and appendages. In addition, embodiments may be provided to orient principal forces exerted by strap systems of the embodiments at any desirable location to treat knee infirmities.

For explanatory purposes, the knee brace embodiment described herein is divided into sections which are denoted by general anatomical terms for the human body. Each of these terms is used in reference to a human leg which is divided in similar sections with a proximal-distal plane generally extending along the meniscus of the knee between the femur and tibia. Any axis formed along the proximal-distal plane, or any plane parallel thereto, from the anterior to the posterior, as defined below, can be considered to be an "anteroposterior" axis within the context of this application and which has its ordinary meaning and refers to an axis extending from the anterior to the posterior.

The embodiment of the knee brace is also divided into anterior and posterior sections by an anterior-posterior plane. The anterior-posterior plane generally corresponds to the coronal or frontal plane of a human leg. Each of the anterior and posterior sections is further divided about the center of the knee by a transverse or proximal-distal plane and median, sagittal or lateral-medial planes. Thus, the term "lateral" further has its ordinary meaning and refers to a location lying at or extending toward the right or left side, away from the median plane of the knee. Additionally, the term "medial" has its ordinary meaning and refers to a location lying or extending toward the median plane of the knee. The anatomical terms described herein are not intended to detract from the normal understanding of such terms as readily understood by one of ordinary skill in the art of orthotics.

The terms "rigid," "flexible," and "resilient" may be used herein to distinguish characteristics of portions of certain features of the orthopedic device. The term "rigid" is intended to denote that an element of the device is generally devoid of flexibility. Within the context of support members, frame members, or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members, frame members, or shells that provide support and are freestanding, however such support members, frame members, or shells may have some degree of flexibility or resiliency.

B. Detailed Description of a Knee Brace

As discussed above, the embodiment of the knee brace disclosed herein may be of an unloading, osteoarthritic knee brace of a type generally described in U.S. Pat. Nos. 7,198, 610 and 5,277,698. Accordingly, the description herein focuses on the structure, materials, and configuration of a particular embodiment of an unloading, osteoarthritic knee brace, without belaboring the particular effects and modalities for treating osteoarthritis in the knee joint.

In an exemplary embodiment, as seen in FIG. 1, an unloading, osteoarthritic knee brace 10 includes first and second (proximal and distal) frame members 12, 14. The frame members may be formed of any suitable material and in any suitable geometry such that the frame members provide sufficient support to the limb, as will be recognized by a skilled artisan. The frame members may in the form of shells, struts, lattice work, or any other suitable configurations that at least partially surround and support a portion of the wearer's anatomy. The frame members may be formed so as to be rigid, semi-rigid, flexible, or resilient, or any suitable combination thereof. Exemplary materials include, but are not limited to, plastics such as polyethylene and polystyrene, carbon fiber and epoxy composites, and glass fiber and epoxy composites. It will be recognized that suitable padding may be provided along the interior shell surfaces in order to aid with user comfort As will be recognized by the skilled artisan, the frame members 12, 14 will have or define an open configuration to allow the thigh region 22 and the shin or calf region 26 of the leg 20 to be encompassed within the respective shell portions 12, 14. It will further be recognized that any suitable configuration of retaining mechanism may be provided to maintain the knee brace 10 in position on the leg 20. Such retaining mechanisms may include straps utilizing hook and loop fasteners, buckles, snaps, and other recognized retaining structures. Exemplary retaining mechanisms are described in detail in U.S. Pat. No. 7,198,610. Such retaining mechanisms may adjustably connect to the proximal and distal frame members 12, 14 at connection points 48 to secure the respective frame members to the thigh and calf regions 22, 26.

In the exemplary embodiment, the proximal and distal shell portions 12, 14 each include an extending portion along a first side thereof. While this extending portion is shown along the lateral side of the knee brace 10 in FIG. 1, it will be recognized that the extending portions may be alternately or also provided along a medial side thereof. It will also be recognized that the proximal and distal shell portions 12, 14 may be formed without such an extending portion.

A flexion-extension hinge 30 connects between the proximal and distal frame members 12, 14 in order to provide flexion and extension to the knee brace 10 and the leg 20 to which the brace is secured. In the exemplary embodiment, the flexion-extension hinge 30 connects between the extending portions of the proximal and distal frame members 12, 14. The hinge 30 allows the leg to move in flexion and extension throughout the gait cycle. The hinge 30 also provides the counteracting forces to keep the proximal and distal frame members from collapsing together when the stability straps described below are tightened.

The hinge 30 may be a monocentric or polycentric hinge, as will be recognized by the skilled artisan. Exemplary hinges are described in U.S. Pat. No. 5,302,169, granted Apr. 12, 1994, and U.S. Pat. No. 7,201,728, granted Apr. 10, 2007, both incorporated herein in their entirety by reference. The hinge 30 may also include flexion-extension stops to limit the amount of flexion or extension of the brace.

The hinge 30 includes upright members that provide support to the knee brace 10 and provide the connection points between the hinge 30 and the proximal and distal frame members 12, 14. In a typical knee brace, the upright members are substantially rigid or slightly resilient in order to provide support to the brace. The uprights may be in any suitable configurations, such as elongated struts, frame or lattice work, or any other suitable configuration for connecting the frame members 12, 14 to a flexion-extension hinge.

In the exemplary embodiment shown in FIG. 1, the upright members are divided into proximal and distal hinge supports 32, 34 and proximal and distal frame supports 36, 38. Each of the supports 32, 34, 36, 38 may be formed in a substantially rigid or slightly resilient configuration utilizing specific geometries and materials, including, but not limited to, metals, such as aluminum or steel alloys, plastics, or carbon or glass fiber and epoxy composites. In a variation, the frame supports may be integrally formed with the shell portions.

Figure 2:
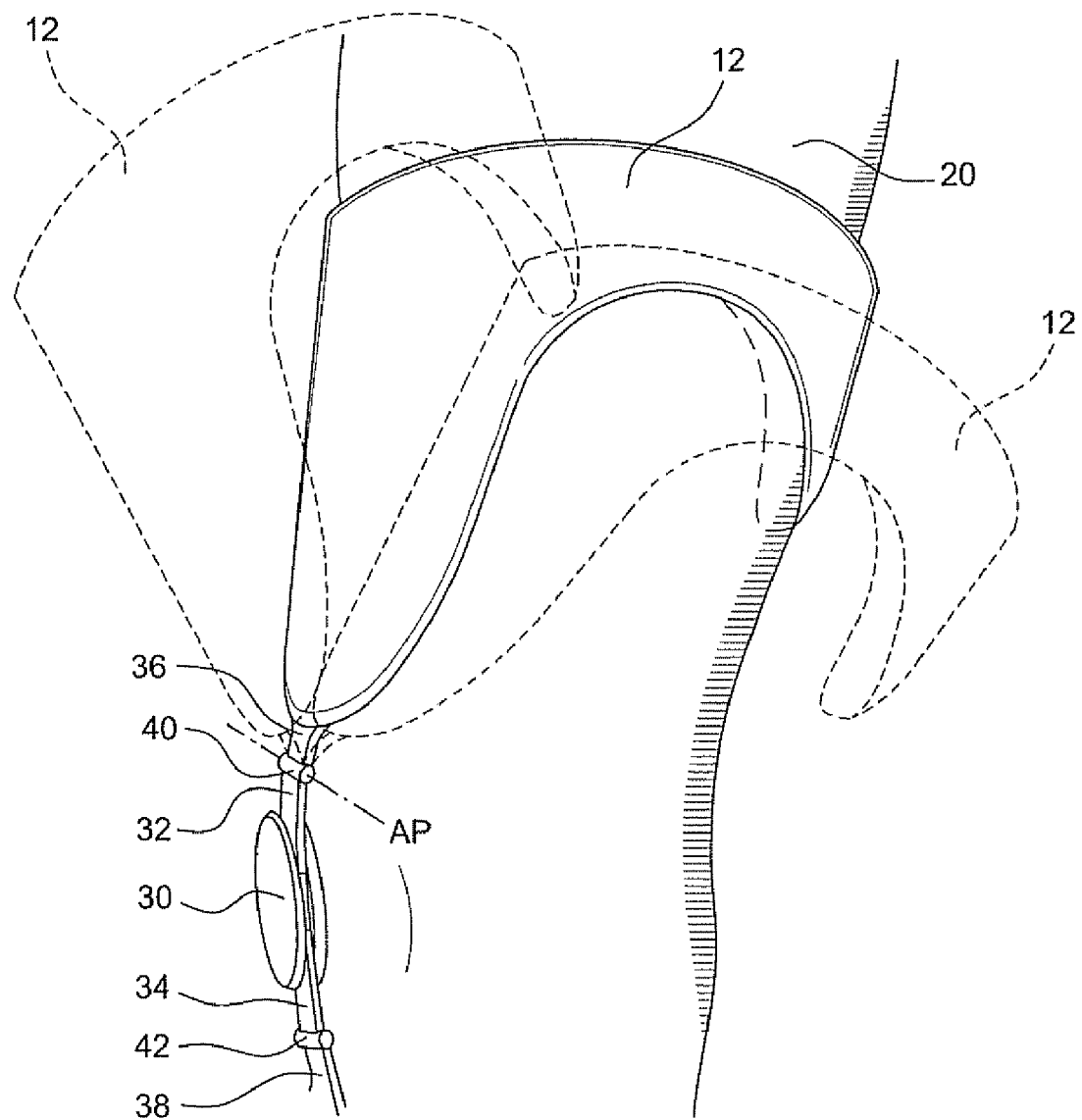
FIG. 2 is a partial view of the knee brace of FIG. 1 showing the proximal shell in various lateral and medial rotated positions with respect to the flexion-extension hinge member.
Figure 3:
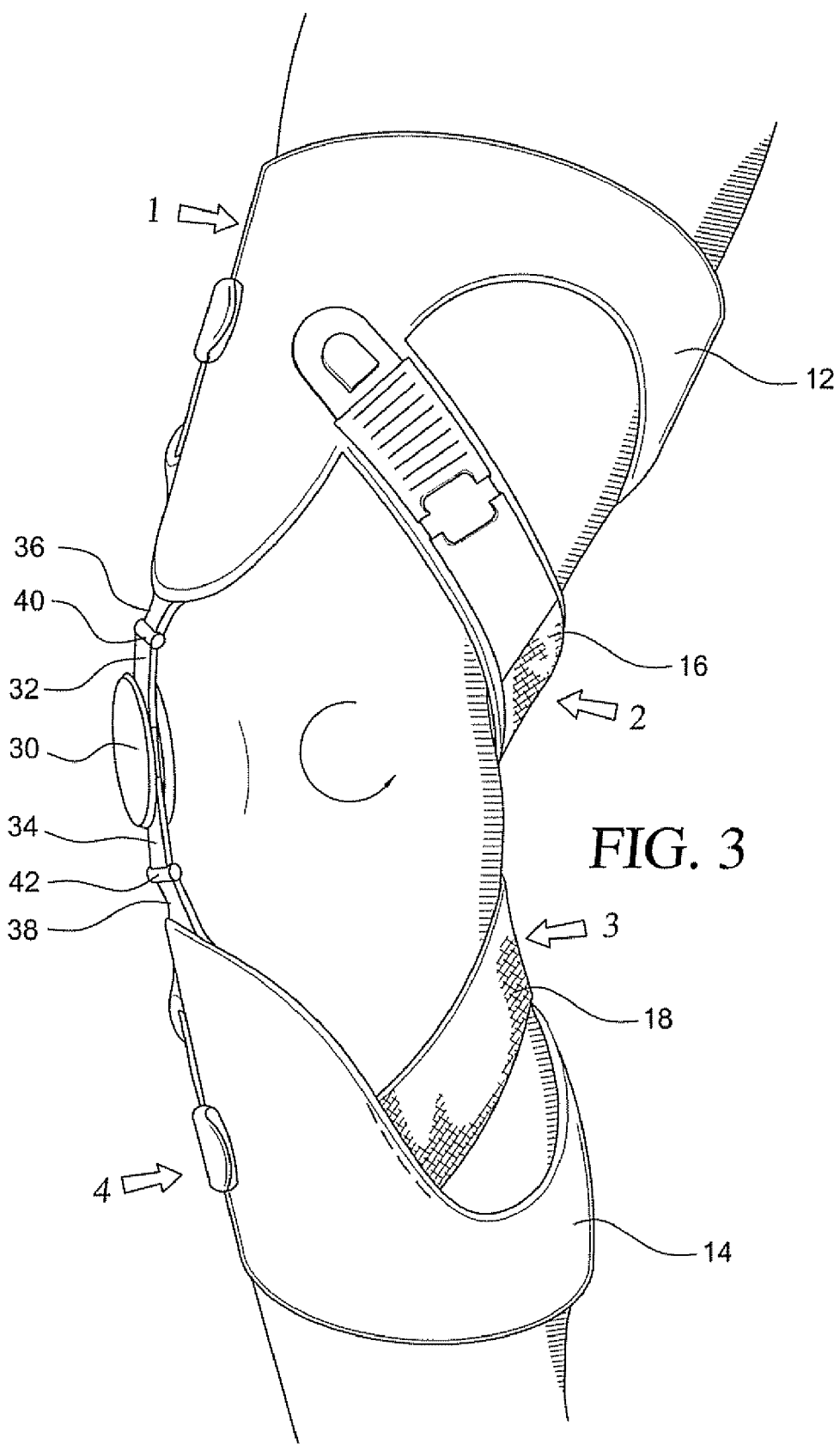
FIG. 3 is a front perspective view of the knee brace of FIG. 1 showing a different degree of varus rotation of the knee as applied by the knee brace.

As shown in FIGS. 1-3, proximal and distal articulating portions in the form of free hinges 40, 42 are positioned between the proximal frame and hinge supports 36, 32 and the distal frame and hinge supports 38, 34. In a variation, the frame supports may be the frame member itself, such that the free hinges 40, 42 are connected directly to the proximal and distal frame members 12, 14. Any suitable mechanism that allows free rotation within a predetermined range of motion about an anteroposterior axis between the proximal frame and hinge supports 36, 32 and the distal frame and hinge supports 38, 34 may be utilized. Of course, as previously mentioned, the free hinges may also allow rotation about the proximal-distal axis, or any other suitable or desired rotation. Exemplary articulating free hinges are discussed in detail below.

As exemplified in FIG. 2, the articulating free hinge 40 allows the proximal frame member 12 to freely rotate within a predetermined range of motion about an anteroposterior axis AP with respect to the hinge 30, when the brace 10 is not positioned on the leg 20. Similarly, the articulating free hinge 42 allows the distal frame member 14 to freely rotate about an anteroposterior axis with respect to the hinge 30, when the brace 10 is not positioned on the leg 20. When the brace 10 is positioned on the leg, the free hinges 40, 42 still allow the proximal and distal frame members 12, 14 to rotate, however, the leg 20 must also change its alignment to move with the proximal and distal frame members 12, 14. In this manner, the varus/valgus angle of the knee may be adjusted.

Further, as also shown in FIG. 2, and unexpectedly, the flexion-extension hinge 30 does not compress or bind when the proximal and distal frame members 12, 14 rotate about an anteroposterior axis. Instead, the hinge 30 maintains its position while allowing the proximal and distal frame members 12, 14 to freely rotate without locking about the hinge 30. Thus, the varus/valgus angle of the knee can be adjusted, as will be discussed in detail below.

Returning to FIG. 1, the knee brace 10 also includes proximal and distal stability straps 16, 18. The stability straps 16, 18 are connected to the proximal and distal frame members 12, 14 at connection points 28. The stability straps 16, 18 are selectively adjustable to provide a varus or valgus three point pressure moment on the leg through the variable stability strap forces AA and BB along the direction of the stability straps in a manner that is described in detail in U.S. Pat. No. 7,198,610. Exemplary adjusting mechanisms include ratchet mechanisms, or slotted D-ring and straps utilizing hook and loop fasteners, as will be recognized by a skilled artisan. A single spiraling stability strap may be utilized to the same effect in place of the two illustrated stability straps.

As further shown in FIG. 1, once the stability straps are tightened to a certain degree, a varus/valgus moment M is applied to the knee region 24. Further, the proximal and distal frame members 12, 14 want to collapse together. This tendency to collapse manifests compressive forces A and B that are transmitted through the free hinges 40, 42 and offset by force C within the hinge 30. Since the compressive forces A and B are offset, such the hinge 30 does not compress and bind up or alter its configuration. Thus, unexpectedly, the hinge 30 maintains its position, such that the assembly of the hinge 30 and the proximal frame and hinge supports 36, 32 and the distal frame and hinge supports 38, 34 feels substantially rigid and provides sufficient stability and support to the leg 20. The hinge 30 of course continues to allow flexion and extension, even while the assembly provides the necessary support to the leg.

The fact that such an assembly, which includes both the proximal and distal free hinges 40, 42, provides sufficient rigidity or support and stability to the knee joint is an unexpected result. Further, the fact that such a single assembly aligned along a lateral or medial side of the leg only is sufficient to provide the necessary support to the leg and knee joint is also an unexpected result. Common sense would seem to dictate that the inclusion of such free hinges 40, 42, without the use of an opposed substantially rigid strut or support would eliminate the necessary support for the leg and joint by allowing the frame members and flexion-extension hinge to collapse upon each other or to bind up.

The varus/valgus moment M discussed above manifests via the lateral-medial forces 1, 2, 3, 4, which are offset along the leg 20 at the points where the proximal and distal frame members 12, 14 and the proximal and distal stability straps 16, 18 contact the lateral and medial sides of the leg 20.

As previously mentioned, the articulating free hinges 40, 42 allow the proximal and distal frame members 12, 14 to freely rotate within a predetermined range of motion with respect to the hinge 30. Once the brace 10 is positioned on the leg, however, the thigh and calf regions 22, 26 must move with the proximal and distal frame members 12, 14 in order for the frame members to move. Accordingly, if the alignment of the leg does not change, the proximal and distal frame members 12, 14 cannot move into varus/valgus and the upright assembly, including the flexion-extension hinge 30 and the free hinges 40, 42, thus feels substantially rigid against the leg, while still allowing for flexion and extension of the leg. Since the thigh and calf regions 22, 26 move with the proximal and distal frame members 12, 14, any desired amount of varus/valgus rotation of the knee region 24 can be obtained As shown in FIG. 1, once the stability straps 16, 18 have been tightened, the proximal and distal frame members 12, 14 become fixed, along with the leg 20, such that the articulating free hinges 40, 42 do not allow free movement of the frame members unless the leg portions also move with the frame members. Thus, unexpectedly, the upright assembly including the hinge 30 and the free hinges 40, 42, maintains its position and feels substantially rigid against the leg, rather than altering its position and creating instability or binding-up to prevent flexion and extension. The hinge 30 does move to closely conform to the leg when the alignment of the leg changes throughout the gait cycle.

As exemplified in FIG. 3, the varus/valgus angle of the knee and leg that is provided by the rotation of the frame members 12, 14 about the free hinges 40, 42 can be altered further by adjusting the tension in the stability straps 16, 18. Again, once the stability straps 16, 18 have been tightened, the frame members 12, 14 achieve a stable varus/valgus configuration such that the upright assembly including the hinge 30 and the free hinges 40, 42, feels rigid on the leg, while still allowing flexion and extension of the leg.

Accordingly, even though there are free articulating pivot points or flex points 40, 42 in the uprights between the hinge 30 and the frame members 12, 14, once the brace 10 is positioned on the leg and the stability straps 16, 18 are tightened, the hinge assembly 30 and uprights form a substantially rigid support for the leg, while the hinge 30 allows flexion and extension. The varus/valgus angle of the knee can be adjusted by tightening or loosening the stability straps 16, 18 in order to allow the leg 20 and frame members 12, 14 to rotate about an anteroposterior axis via the free hinges 40, 42 with respect to the hinge 30, until a stabilized configuration is reached such that the hinge assembly 30 and uprights again feel rigid against the leg. This function occurs due to the use of a single free point above and a single knee point below the hinge 30. If two free points were used above and below the hinge, the frame members could collapse or compress together and thus would diminish the function of the brace.

As previously discussed, such a result is contrary to expectations, since a skilled artisan would have expected a flexion-extension hinge using proximal and distal free flex or pivot points to shift positions or compress and bind-up when the brace is positioned on the leg. Instead, the exemplary configuration provides an orthopedic device that allows for great variation in the amount of varus/valgus angle applied to the leg, while still providing a stable support and an upright assembly that feels substantially rigid throughout the gait cycle even though proximal and distal free flex or pivot points are utilized.

Exemplary configurations of articulating free hinges are discussed below.

C. Various Configurations of Articulating Free Hinges

A first variation of a hinge assembly utilizing articulating portions in the form of free hinges is shown in FIGS. 4 and 5. A flexion-extension hinge 50 includes proximal and distal hinge struts or supports 52, 54. Proximal and distal frame struts or supports 56, 58 are also provided. The proximal and distal frame struts or supports 56, 58 may be integrally formed with the proximal and distal hinge struts or supports 52, 54 and cut or milled into separate pieces, or they may be separately formed. Suitable materials are discussed above with respect to the uprights of the knee brace 10.

Proximal and distal articulating free hinges 60, 62, seen in FIG. 5, are positioned between the proximal and distal frame supports 56, 58 and the proximal and distal hinge supports 52, 54. The free hinges 60, 62 may be formed by overmolding a flexible or resilient material, such as plastic, in the gaps between the proximal and distal frame supports 56, 58 and the proximal and distal hinge supports 52, 54. Overmolding techniques and materials, such as those described in U.S. provisional patent application No. 60/900,719, filed Feb. 12, 2007, and incorporated herein in the entirety by reference, may be utilized in order to create the free hinges and uprights.

The overmolded free hinges 60, 62 will encompass at least a portion of the proximal and distal shell supports 56, 58 and the proximal and distal hinge supports 52, 54, as it is necessary to provide surfaces onto which the free hinges 60, 62 are overmolded.

In a variation, as seen in FIGS. 6 and 7, a flexion-extension hinge 70 includes proximal and distal hinge struts or supports 72, 74. Proximal and distal frame struts or supports 76, 78 are also provided. The proximal and distal frame struts or supports 76, 78 may be integrally formed with the proximal and distal hinge struts or supports 72, 74 and cut or milled into separate pieces, or they may be separately formed. Suitable materials are discussed above with respect to the uprights of the knee brace 10.

Similarly to the variation just discussed, as shown in FIG. 7, overmolded free hinges 80, 82 are provided in the gaps between the proximal and distal shell supports 76, 78 and the proximal and distal hinge supports 72, 74.

In order to provide more surface area for the overmolded material to adhere to, as shown in FIG. 6, holes 84 awe bored, drilled, cast, injection molded, or otherwise formed in the proximal and distal frame supports 76, 78 and the proximal and distal hinge supports 72, 74.

Figure 6A:
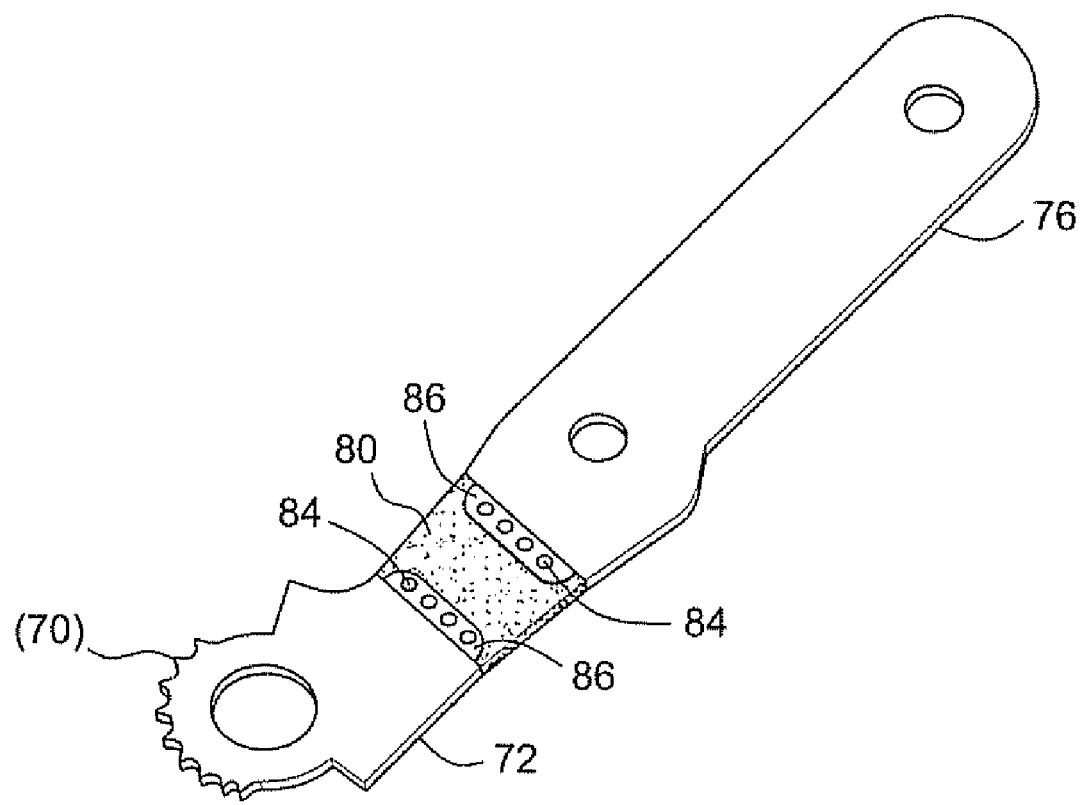
FIG. 6A is a side perspective view of a variation of the proximal part of a hinge assembly for use with the knee brace of FIG. 1 or FIG. 13.

A variation of the free hinge of FIG. 6 is shown in FIG. 6A. While the free hinge 80 of FIG. 6A is shown incorporated into the proximal frame support 76 and the proximal hinge support 72, it will be understood that this configuration of the free hinge 80 can be utilized in either the proximal or distal free hinge position.

As shown in FIG. 6A, the free hinge 80 is formed in an overmolded manner, as discussed herein. In order to provide sufficient strength of adhesion between the overmolded free hinge 80 and the supports 76, 72, flange portions 86 extend from the distal and proximal ends of the supports, respectively. Holes 84 are bored through the flange portions 86 in order to provide further surface area for adhesion of the overmolded material to the supports 76, 72.

Further variations of hinge assemblies are shown in FIGS. 8-10. Flexion-extension hinge 90 includes proximal and distal hinge supports 92, 94. Proximal and distal free hinges 96, 98 are connected to the proximal and distal hinge supports 92, 94.

As shown in FIG. 8, the proximal and distal hinge supports 92, 94 have a substantially planar configuration.

In a variation, as seen in FIG. 9, the proximal and distal hinge supports 92, 94 have a bent configuration. In this manner, the hinge assembly may better conform to the geometry of the knee joint and leg.

The components of the hinge assembly of FIG. 8 are shown in an exploded view in FIG. 10. The proximal and distal free hinges 96 and 98 are composed of a number of elements. First connection members 100 connect to the proximal and distal hinge supports 92, 94 via connectors 112, which may be rivets, screws, welds, snap connections, or any other suitable connectors.

A clearance hole 104 is defined horizontally through a first end and a first side of the first connection member 100. Second connection members 102 are correspondingly shaped to engage the first end and first side of the first connection members 100. The second connection members include a threaded hole 106 defined in a first end and a first side thereof, such that a pivot pin 108 passes through the clearance hole 104 and is threaded into the threaded hole 106. In order to provide relative free rotation of the first and second connection members 100, 102, a biasing member 110, such as a spring, is provided between the threaded hole 106 and the clearance hole 104 to bias the contacting surfaces of the threaded and clearance holes 106, 104 away from each other.

The second connection members 102 are connected to proximal and distal shell supports utilizing any suitable connection mechanism, similar to connector 112.

The components of the hinge assembly of FIGS. 8-10 may be formed from any suitable material, such as metals or plastics. For example, all of the components may be injection molded plastics which may be snap fit together to form the hinge assembly.

Figure 11:
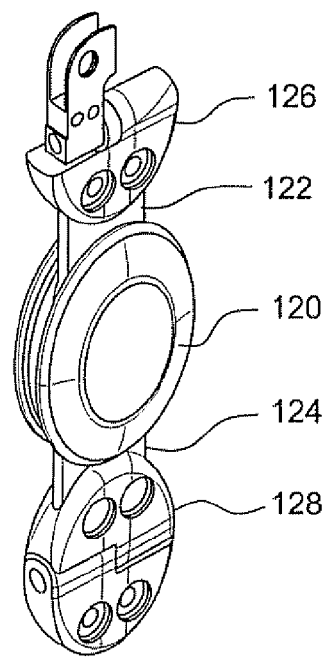
FIG. 11 is a perspective view of yet another variation of the hinge assembly of FIG. 8.
Figure 12:
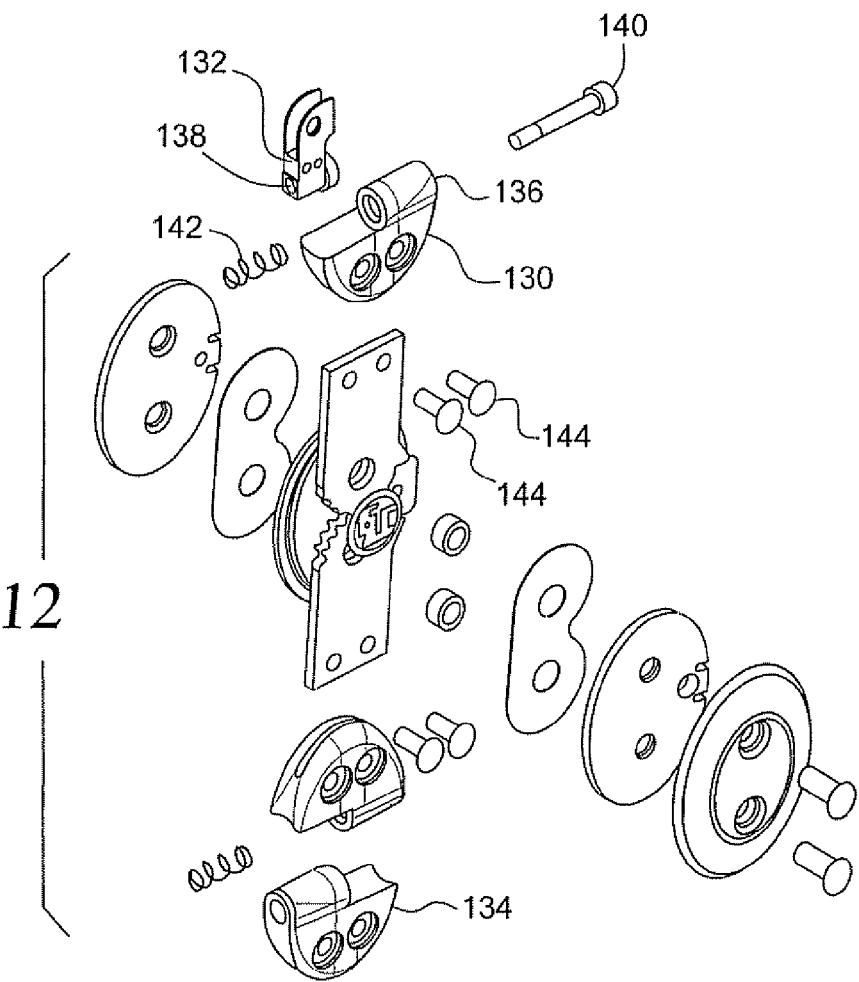
FIG. 12 is an exploded view of the hinge assembly of FIG. 11.

For example, in the variation of a hinge assembly as shown in FIGS. 11 and 12, components may be snap fit together. The flexion-extension hinge 120 includes proximal and distal hinge supports 122, 124. Proximal and distal free hinges 126, 128 are connected to the proximal and distal hinge supports 122, 124.

The components of the hinge assembly of FIG. 1 are shown in an exploded view in FIG. 12. The proximal and distal free hinges 126 and 128 are composed of a number of elements. First connection members 130 connect to the proximal and distal hinge supports 122, 124 via connectors 144, which may be any suitable connectors, as discussed above.

A clearance hole 136 is defined horizontally through a first end and a first side of the first connection member 130. Second connection members 132 are correspondingly shaped to engage the first end and first side of the first connection members 130. The second connection members include a threaded hole 138 defined in a first end and a first side thereof, such that a pivot pin 140 passes through the clearance hole 136 and is threaded into the threaded hole 138. As discussed above a biasing member 142, such as a spring, is provided between the threaded hole 138 and the clearance hole 136 to bias the contacting surfaces of the threaded and clearance holes 138, 136 away from each other.

As an added variation, one or both of the proximal and distal free hinges 126 and 128 may be locked against free rotation in order to provide medial-lateral stability when necessary. Such locking can occur by any known mechanism, including, but not limited to, the mechanisms disclosed in U.S. Pat. No. 5,302,169.

In such circumstances, the brace using the hinge assembly of FIGS. 11 and 12 can be positioned on the leg with the free hinges 126, 128 unlocked. The stability straps can then be tightened to obtain the desired amount of varus/valgus rotation. One or both of the free hinges 126, 128 can then be locked to provide added medial-lateral stability.

Returning to the hinge components, the second connection members 122 include a cap member 134 that snap fits onto the second connection member. Both the cap member 134 and the second connection members 122 are connected to proximal and distal shell supports utilizing any suitable connection mechanism, similar to connector 144.

It will be recognized that any of the described variations, or equivalent, free hinge configurations may be utilized in an orthopedic brace according to this disclosure.

D. Detailed Description of a Variation of a Knee Brace

Figure 13:
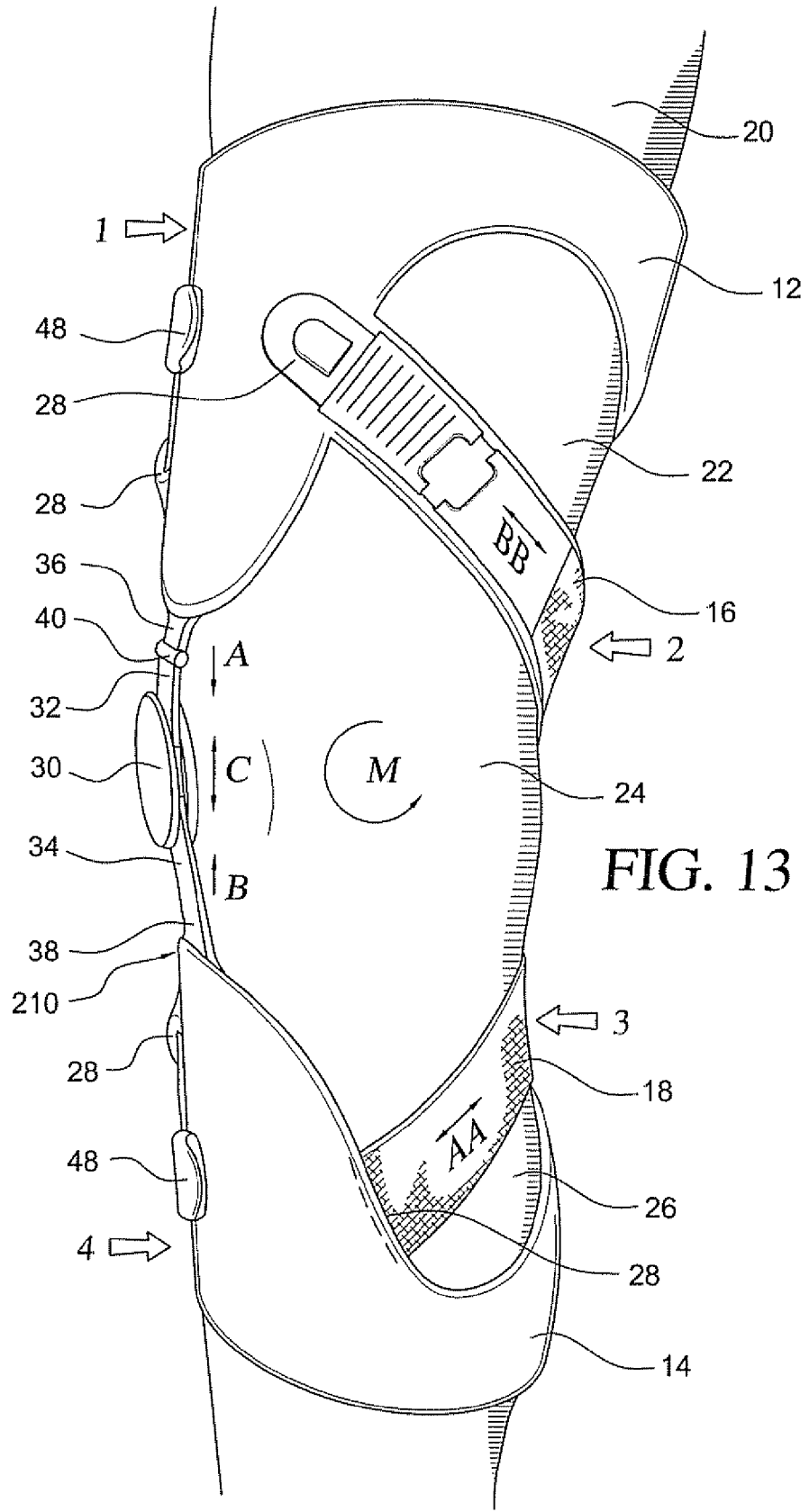
FIG. 13 is a variation of the knee brace of FIG. 1 that utilizes a single free hinge assembly.

A variation of the knee brace of FIG. 1 is shown in FIG. 13. The knee brace 210 of FIG. 13 has the same essential configuration as the knee brace 10 of FIG. 1, and the same reference numerals describe similar or the same components.

The knee brace 210 of FIG. 13 utilizes a single proximal articulating free hinge 40. The free hinge can be constructed in any manner described herein. In contrast to the knee brace 10, the knee brace 210 utilizes either a distal upright with no distal free hinge, or a distal hinge that is oriented with the desired varus/valgus angle and locked as described above. Such a lockable hinge can provide additional medial-lateral stability, while the proximal free hinge 40 provides adaptability to the knee brace 210, in a manner previously described.

Thus, the knee brace 210 provides the added benefits of utilizing a free hinge to promote adjustability and adaptability, while retaining the benefits of additional rigidity by utilizing a standard strut support or a lockable hinge.

While the free hinge 40 is shown in the proximal position in the knee brace 210, it will be understood that the orientations of the free hinge and the strut or lockable hinge may be alternated, such that a distal free hinge is provided and a proximal strut with no proximal free hinge, or a proximal hinge that is oriented with the desired varus/valgus angle and locked as described above.

E. Conclusion

While a particular embodiment of an orthopedic device is discussed above utilizing injection molded parts, the components of the knee brace described herein may be formed in any suitable manner recognized by a skilled artisan, such as casting, machining, stereolithography, or any other suitable process.

The disclosed embodiment of an orthopedic device provides an improved knee brace that has a lower profile than a typical brace, and further allows for a great variation in varus/valgus rotation of the knee joint by utilizing free hinges.

It is understood that the size of the brace and the components thereof can be adjusted so that a large number of different users having different sized joints and body parts may benefit from the present design.

It is also understood that the locations of the various connection points can be alternated from those shown, such that the connection points may be altered from the positions as illustrated herein.

Of course, it is to be understood that not necessarily all objects of advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct a knee brace in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

We claim:

1. An orthopedic device having opposed first and second sides along an anterior-posterior plane, the device comprising:
   first and second shells arranged to secure about anatomical portions of a wearer;
   first and second uprights connecting respectively to the first and second shells, and located only on the first side of the device; and
   a hinge connecting to the first and second uprights, the hinge permitting movement of the first and second shells relative to one another into flexion and extension;
   wherein at least one of the first and second uprights includes a first articulating portion permitting the at least one of the first and second uprights and the respective first or second shell connected thereto to freely rotate generally about an anteroposterior axis with respect to the hinge; and
   wherein a first stability strap connecting to the first and second shells is selectively adjustable to rotate the at least one of the first and second uprights and the respective first or second shell connected thereto a predetermined amount about the first articulating portion and the first stability strap is further arranged to exert a first force passing through the first articulating portion that is offset by an opposed force created within the hinge, and a second stability strap connecting to the first and second shells is selectively adjustable to rotate the other of the at least one of the first and second uprights and the respective first or second shell connected thereto about the second articulating portion and the second stability strap is further arranged to exert a second force passing through the second articulating portion that is offset by an opposed force created within the hinge when the device is in use by a wearer;
   wherein the first and second stability straps exert the first and second forces from the second side of the brace;
   wherein a clearance is formed between the first and second frame members along the second side of the brace.

2. The orthopedic device according to claim 1, further comprising:
   wherein at the other of the least one of the first and second uprights includes a second articulating portion permitting the other of the at least one of the first and second uprights and the respective first or second shell connected thereto to freely rotate generally about an anteroposterior axis with respect to the hinge.

3. The orthopedic device according to claim 2, wherein the first or second articulating portion comprises:
   a hinge support portion connecting to the hinge; and
   a shell support portion connecting to a respective one of the first or second shells;
   wherein the first or second articulating portion connects the hinge and shell support portions.

4. The orthopedic device according to claim 3, wherein the articulating portion is an overmolded portion encompassing at least a portion of each of the hinge and shell support portions.

5. The orthopedic device according to claim 2, wherein the first or second articulating portion comprises:
   a hinge support portion connecting to the hinge;
   a shell support portion connecting to a respective one of the first or second shells; and
   a pivoting portion connecting the hinge and shell support portions.

6. The orthopedic device according to claim 5, wherein the pivoting portion comprises:
   a first connection member connecting to the hinge support portion;
   a second connection member connecting to the shell support portion; and
   a pivot pin connecting the first and second connection members in a freely pivotable manner.

7. An orthopedic device having opposed first and second sides along an anterior-posterior plane, the device comprising:
   first and second frame members arranged to secure about anatomical portions of a wearer;
   first and second uprights connecting respectively to the first and second frame members, and located only on the first side of the device; and
   a hinge connecting the first and second uprights, the hinge permitting movement of the first and second frame members relative to one another into extension and flexion;
   wherein at least one of the first and second uprights includes a single articulating portion permitting the at least one of the first and second uprights and the respective first or second frame member connected thereto to freely rotate at least within a range of 90 degrees generally about an anteroposterior axis with respect to the hinge;
   at least one stability strap connecting to the first and second frame members, and selectively adjustable to rotate the first or second frame member about the articulating portion and is arranged to extend along the second side of the brace and exert a force directed toward the first side of the brace by passing through the first articulating portion that is offset by an opposed force created within the hinge when the device is in use by a wearer;
   wherein a clearance is formed between the first and second frame members along the second side of the brace.

8. The orthopedic device according to claim 7, wherein at least one of the first and second uprights comprises:
   a hinge support portion connecting to the hinge;
   a frame member support portion connecting to a respective one of the first and second frame members; and
   the articulating portion located between the hinge support portion and the frame member support portion and connecting the hinge and frame member support portions.

9. The orthopedic device according to claim 8, wherein the articulating portion is an overmolded portion encompassing at least a portion of each of the hinge support portion and the frame member support portion.

10. The orthopedic device according to claim 8, wherein the articulating portion comprises:
    a first connection member connecting to the hinge support portion;
    a second connection member connecting to the frame member support portion; and
    a pivot pin connecting the first and second connection members in a freely pivotable manner.

11. The orthopedic device according to claim 7, wherein the first and second frame members are first and second shell portions.

12. A method of supporting an anatomical portion of a wearer comprising the steps of:
    providing an orthopedic device having opposed first and second sides along an anterior-posterior plane, and comprising:
    first and second frame members arranged to secure about anatomical portions of a wearer;
    first and second uprights connecting respectively to the first and second frame members and located only on the first side of the device;
    and
    a hinge connecting to the first and second uprights, the hinge permitting movement of the first and second frame members relative to one another into flexion and extension;
    wherein at least one of the first and second uprights includes a first articulating portion permitting the at least one of the first and second uprights and the respective first or second frame member connected thereto to freely rotate generally about an anteroposterior axis with respect to the hinge; and
    wherein a first stability strap connecting to the first and second frame members is arranged to secure about anatomical portions of a wearer and is selectively adjustable to rotate the at least one of the first and second uprights and the respective first or second frame member connected thereto about the first articulating portion;
    arranging the orthopedic device about anatomical portions of a wearer; and
    adjusting the first stability strap to provide a predetermined amount of rotation to the at least one of the first and second uprights and the respective first or second frame member connected thereto about the first articulating portion to create a force passing through the first articulating portion from the second side of the brace that is offset by an opposed force created within the hinge;
    wherein a clearance is formed between the first and second frame members along the second side of the brace.

13. The method according to claim 12, further comprising the step of:
    providing an orthopedic device wherein the other of the least one of the first and second uprights includes a second articulating portion permitting the other of the at least one of the first and second uprights and the respective first or second frame member connected thereto to freely rotate generally about an anteroposterior axis with respect to the hinge.

14. The method according to claim 13, further comprising the steps of:
    providing an orthopedic device having a second stability strap connecting to the first and second shells, which is selectively adjustable to rotate the other of the at least one of the first and second uprights and the respective first or second frame member connected thereto about the second articulating portion; and adjusting the second stability strap to provide a predetermined amount of rotation to the other of the at least one of the first and second uprights and the respective first or second frame member connected thereto about the second articulating portion to create a force passing through the second articulating portion from the second side of the brace that is offset by an opposed force created within the hinge.

15. The method according to claim 13, further comprising the steps of:
providing an orthopedic device wherein the first or second articulating portion includes:
a hinge support portion connecting to the hinge;
a frame member support portion connecting to a respective one of the first or second frame member; and
the first or second articulating portion connecting the hinge and frame member support portions.

16. The method according to claim 15, further comprising the step of:
providing an orthopedic device, wherein the articulating portion is an overmolded portion encompassing at least a portion of each of the hinge and frame member support portions.

17. The method according to claim 13, further comprising the step of:
providing an orthopedic device wherein the first or second articulating portion includes:
a hinge support portion connecting to the hinge;
a frame member support portion connecting to a respective one of the first or second frame members; and
a pivoting portion connecting the hinge and frame member support portions.

18. The method according to claim 17, further comprising the step of:
providing an orthopedic device wherein the pivoting portion comprises:
a first connection member connecting to the hinge support portion;
a second connection member connecting to the frame member support portion; and
a pivot pin connecting the first and second connection members in a freely pivotable manner.

\* \* \* \* \*